(12) United States Patent
Pitsch et al.

(10) Patent No.: US 9,534,003 B2
(45) Date of Patent: Jan. 3, 2017

(54) PROTECTED LINKER COMPOUNDS

(71) Applicant: ReseaChem GmbH, Burgdorf (CH)

(72) Inventors: Stefan Pitsch, Stein am Rhein (CH); Stefan Berger, Burgdorf (CH)

(73) Assignee: ReseaChem GmbH, Burgdorf (CH)

( * ) Notice: Subject to any disclaimer, the term of this patent is extended or adjusted under 35 U.S.C. 154(b) by 8 days.

(21) Appl. No.: 14/366,484

(22) PCT Filed: Dec. 19, 2012

(86) PCT No.: PCT/CH2012/000276
§ 371 (c)(1),
(2) Date: Jun. 18, 2014

(87) PCT Pub. No.: WO2013/091120
PCT Pub. Date: Jun. 27, 2013

(65) Prior Publication Data
US 2015/0011746 A1    Jan. 8, 2015

Related U.S. Application Data

(60) Provisional application No. 61/578,481, filed on Dec. 21, 2011.

(51) Int. Cl.
| | |
|---|---|
| *C07F 9/24* | (2006.01) |
| *C07H 21/04* | (2006.01) |
| *C07J 43/00* | (2006.01) |
| *C07J 51/00* | (2006.01) |

(52) U.S. Cl.
CPC .......... *C07F 9/2404* (2013.01); *C07F 9/2408* (2013.01); *C07H 21/04* (2013.01); *C07J 43/003* (2013.01); *C07J 51/00* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 2,901,503 A | 8/1959 | Fitch | |
| 7,164,014 B2 | 1/2007 | Huang et al. | |
| 2004/0009982 A1 | 1/2004 | Tohnishi et al. | |
| 2005/0075299 A1* | 4/2005 | Ward ................ | C12N 15/1137 514/44 A |
| 2006/0167240 A1 | 7/2006 | Weiss et al. | |

OTHER PUBLICATIONS

Gali, J. Org. Chem. 2000, 65, 676-680.*
Akiyama, M. et al., N-hydroxy amides. Part 8. Synthesis and Iron (iii)-holding properties of di- and tri-hydroxamic acids extending from benzene-di- and -tri-carbonyl units through oligo (ethyleneoxy) arms, Journal of the Chemical Society, Perkin Transactions 2, 1989, pp. 1213-1218, No. 9, XP055058202.
Hickman, D. T. et al., Design, synthesis, conformational analysis and nucleic acid hybridisation properties of thymidyl pyrrolidine-amide oligonucleotide mimics (POM), electronic supplementary information (ESI) available: experimental details at http://www.rsc.org/suppdata/ob/b3/b306156f/, Organic & Biomolecular Chemistry, 2003, pp. 3277-3292, vol. 1, No. 19, XP055058198, ISSN: 1477-0520.
Kim, J. et al., Discriminating Detection between Mg2+ and Ca 2+ by Fluorescent Signal from Anthracene Aromatic Amide Moiety, Org. Lett., 2007, pp. 4419-4422, vol. 9.
Kim, J. et al., Supporting Information: Discriminating Detection between Mg2+ and Ca2+ by Fluorescent Signal from Anthracene Aromatic Amide Moiety, Division of Environmental Material Science, Graduate School of Environmental Science, Hokkaido University, 2015, pp. S1-S11.
Pitsch, S. et al, Reliable Chemical Synthesis of Oligoribonucleotides (RNA) with 2'O-[(Triisopropylsilyl)oxy]methyl(2'-O-tom)-Protected Phosphoramidites, Helv. Chim. Acta, 2001, pp. 3773-3795, vol. 84.
Mahboobi, S. et al., Syntheses of (RS)-and (S)- (−)-Nazlinin and (RS)- and (+)-6-Azacyclodeca[5,4-b]indol-1-amine, Archiv Der Pharmazie, 1995, pp. 371-376, vol. 328, No. 4, ZP055058199, ISSN: 0365-6233.
Turner, John, Spermine Phosphoramidite: A Potent Modification with Many Applications, The Glen Report, Glen Research, 2012, pp. 1-12, vol. 24, No. 1.
International Search Report dated Apr. 17, 2013 from PCT/CH2012/000276.

* cited by examiner

*Primary Examiner* — Layla Berry
(74) *Attorney, Agent, or Firm* — Larson & Anderson, LLC

(57) ABSTRACT

The invention features protected linker compounds which comprise at one terminus a protected amino group and at another other terminus a phosphorous activating group, such as a phosphoramidite group. These protected linker compounds are introduced chemically at the 5'-end of oligonucleotides for the purpose of preparing 5'-amino modified oligonucleotides. After deprotection, the thereby introduced amino group then allows further modification (e.g. attachment of dyes) or immobilization (on surfaces or beads) of the oligonucleotide. Specifically, the presented amino protecting group is designed to provide such protected linker compounds in a solid form, which facilitates efficient purification by precipitation or crystallization and aliquoting for distribution and storage.

17 Claims, 9 Drawing Sheets

Formula II

FIG. 6
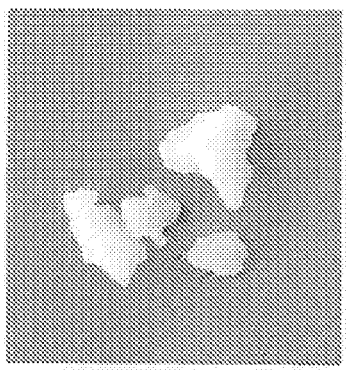
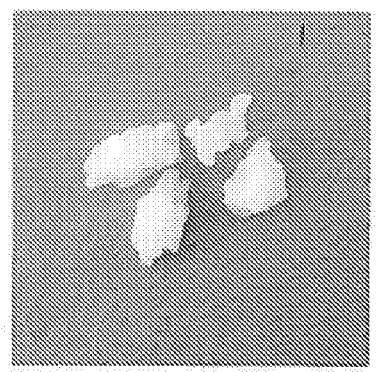
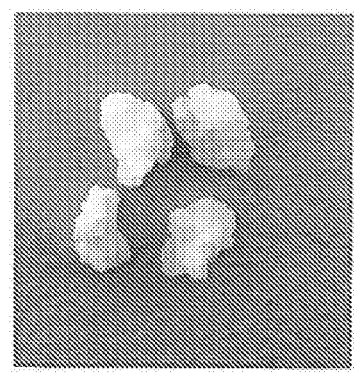
Fig. 6A          Fig. 6B          Fig. 6C

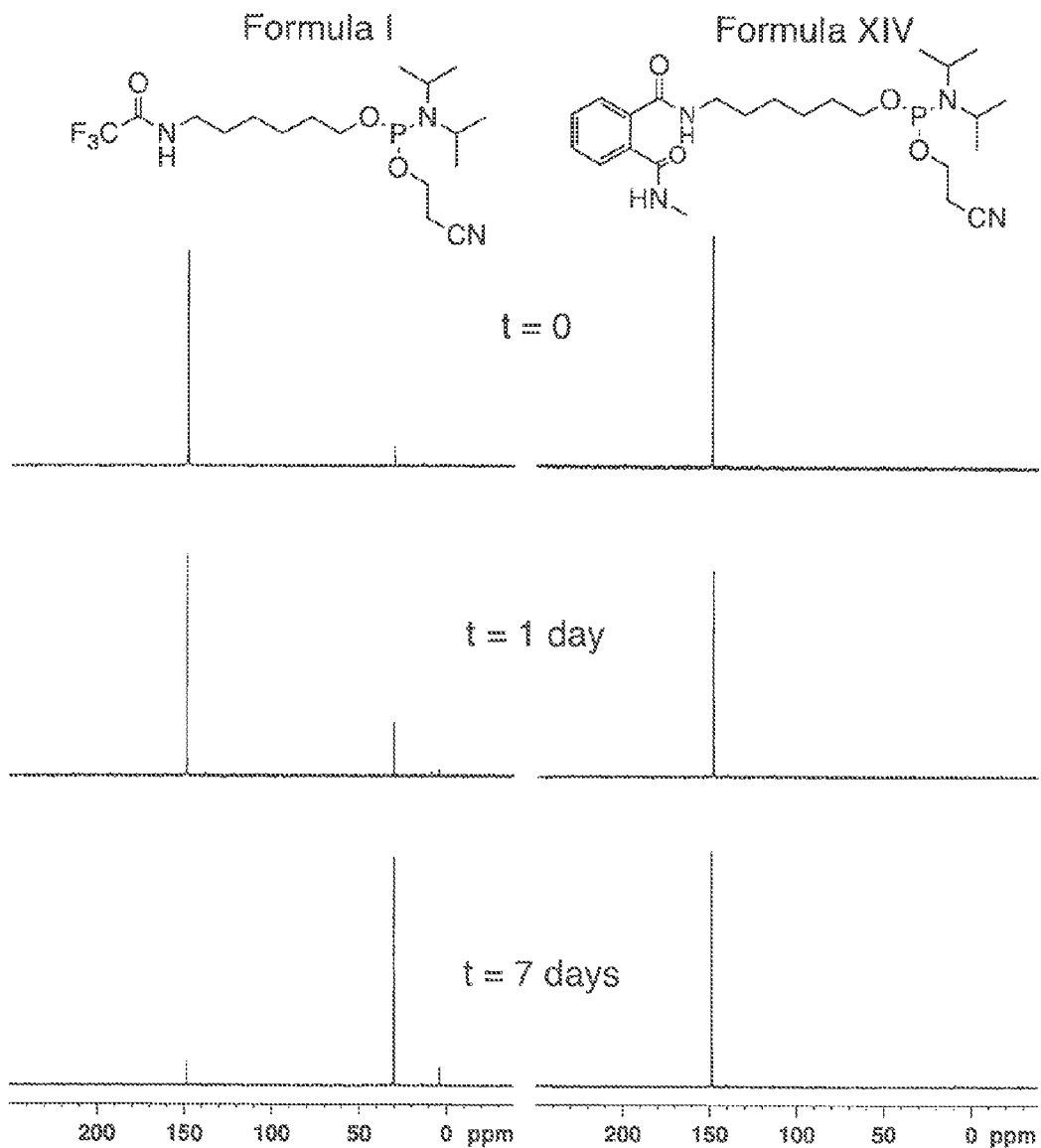

PROTECTED LINKER COMPOUNDS

FIELD OF THE INVENTION

This invention lies in the field of nucleic acid chemistry and relates to protected linker compounds, in particular to protected amino linker compounds and more particularly to protected amino linker phoshoramidite building blocks applicable for the synthesis of 5'-amino functionalized ribo- or deoxyribonucleic acids and derivatives thereof. Furthermore, the invention relates to methods for producing such protected amino linker phoshoramidite building blocks and methods for preparing 5'-amino modified nucleic acids.

BACKGROUND OF THE INVENTION

The chemical synthesis of nucleic acids involves stepwise assembly of suitable, protected phosphoramidite building blocks on solid phase, followed by the removal of protecting groups and the detachment from the solid phase. In addition to the incorporation of ribo- or deoxyribonucleotides, this method allows the introduction of further compounds including nucleotide analogs (containing modified sugar moieties and/or modified nucleobase moieties) as well as other compounds which allow specific detection (e.g. dyes) or specific binding (e.g. biotin). Ideally, the methods for introduction and final deprotection of these further compounds would be identical to methods used for the preparation of the unmodified (physiological) ribo and deoxribo oligonucleotides (RNA and DNA).

However, a variety of useful and routinely employed dyes and reporter groups are not stable under the conditions of assembly and deprotection of oligonucleotides and are therefore introduced post-synthetically by so-called conjugation reactions. Conjugation reactions are also carried out for the immobilization of nucleic acids on surfaces or beads. Such reactions require the presence of a specific chemical group on the oligonucleotide, which has a unique reactivity towards suitably activated dyes/binders or surfaces/beads. These specific chemical groups are usually amino or thiol groups and the materials, required for their introduction into oligonucleotides are called "amino linkers" or "thio linkers", respectively. They typically contain a phosphorous activating group such as a phosphoramidite moiety for the attachment to the nucleic acid, a linker (e.g. alkyl chains or oligoethylenglycol chains of various lengths) and the suitably protected amino or thiol group, respectively.

The presently known amino linker compounds can be divided into two groups. In the first group, the amino protecting group comprises an acid labile mono- or dimethoxytrityl group. These acid labile groups can either be removed before or after removal of the other protecting groups which is carried out by ammonia or various amines. In the latter case, purification of the amino-linker modified nucleic acid can be achieved based on the lipophilic properties of the still present trityl group. Therefore, if purification based on lipophilic properties is desired, amino linkers of this first group are chosen.

The second group of amino linkers is characterized by protecting groups which are cleaved during the deprotection step together with the other protecting groups with ammonia or various amines. Advantageously, for linkers of the second group, no additional deprotection steps are required, and therefore the related manufacturing process is more straightforward. Consequently, they are employed on a much greater scale. In particular, these amino linkers of the second group are used in the high-volume routine and parallel synthesis of amino-modified nucleic acids. The most commonly employed and commercially available amino linkers in this group contain an amino group protected by a trifluoroacetyl group (Formula I), but other protecting groups, such as phthalimide (e.g. Formula XI, see FIG. 3) have been reported [U.S. Pat. No. 7,164,014, Huang et al.].

All known amino linkers of this second type are honey-like, viscous oils. As a consequence they are difficult to handle. For example they can only be purified by chromatography, they are difficult to aliquot in accurate portions and they are difficult to dry. Furthermore, they are quite unstable substances, because they are not stabilized by crystal packing and easily degrade by reaction with oxygen or water. As a consequence, they have to be shipped and stored at low temperatures.

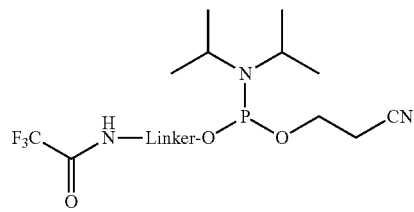

Formula I

Thus, it is an object of the present invention to provide protected linker compounds which overcome disadvantages of this second group of amino linker compounds available in the prior art and which are fully compatible with the standard assembly and deprotection protocols for nucleic acid synthesis. More particular objects of the present invention include to provide such amino linker building blocks which can be purified by precipitation or crystallization, which are easily aliquoted and which do not easily degrade by reaction with oxygen and water.

In a first aspect of the invention, protected amino linker compounds and more particularly protected amino linker phoshoramidite building blocks are provided. In a second aspect, methods of production of amino linker compounds are provided. In a third aspect of the invention, methods of adding a protected amino linker phoshoramidite building block to a previously assembled, protected and immobilized ribo- or deoxyribonucleic acid molecule or to a derivative thereof and methods of deprotecting the protected amino group of the added amino linker compound are provided. The third aspect of the invention also relates to amino functionalized nucleic acids or nucleic acid derivatives comprising an amino protecting group. In a fourth aspect, a use of a diamide substituted protecting group for protecting an amino group is provided. It is in particular the use of a 1,4-diamide group which is covalently bound to an aromatic system, in which two neighbouring C-atoms of an aromatic system are a 2- and a 3-position of the 1,4-diamide amino protecting group (for a detailed definition see Formula II in FIG. 1).

Additional objects and advantages of the invention are set forth in, or will be apparent to those of ordinary skill in the art, from the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of the equivalent means, features, and materials for those shown or discussed, and the functional or positional reversal of various parts, features, method steps, or the like.

Still further, it is to be understood that different embodiments, as well as different presently preferred embodiments, of this invention may include various combinations or configurations of presently disclosed features, elements, method steps, or their equivalents (including combinations of features or configurations thereof not expressly shown in the figures or stated in the detailed description).

These and other features, aspects, and advantages of the present invention will become better understood with reference to the following descriptions and the appended claims. The accompanying drawings, which are incorporated in and constitute a part of this specification, illustrate an embodiment of the invention, and, together with the descriptions, serve to explain the principles of the invention.

SUMMARY OF THE INVENTION

In the first aspect of the invention protected linker compounds, in particular amino linker building blocks suitable for preparing 5' amino-modified oligonucleotides are provided. The amino linker building block comprises a linker, a phosphorous activating group, in particular a phosphoramidite moiety and an amino protecting group. The amino protecting group comprises a 1,4-diamide substructure, with two carbonyl groups comprising a C1 and a C4 carbon atom of the 1,4-diamide and wherein the C1 and C4 carbon atoms are separated by two carbon atoms which are part of an aromatic system and wherein a nitrogen of one of the amide groups constitutes the nitrogen of the protected amino group.

Thus the amino linker building blocks presented here comprise at one end of the linker a diamide amino protecting group and at another end of the linker an activated phosphorous such as a phosphoramidite group. The amino protecting group of the amino linker compound comprises a diamide substructure, in particular a 1,4-diamide substructure, wherein the C-atoms of the carbonyl groups of the 1,4-diamide are separated by two C atoms which are part of an aromatic system. Thus, two carbonyl groups comprising C1 and C4 of the 1,4-diamide are separated by two C-atoms, i.e. C2 and C3, which are part of the aromatic system (see Formula II in FIG. 1). The nitrogen of one of the amide groups constitutes the nitrogen of the protected amino group. This nitrogen is covalently bound to the linker of the amino linker compound. The nitrogen of the other amide group is covalently bound' to one or two alkyl or aryl groups. Thus, the diamide group provides one or two H atoms available for hydrogen bonding with the amid oxygens. This influences the properties of the amino linker compounds presented in this invention. In exemplary embodiments, the presence of two amide oxygens as hydrogen bond acceptors and two N—H hydrogen bond donors in the amino protecting group particularly favors hydrogen bonding.

Amino linker building blocks, wherein the amino protecting group comprises a 1,4-diamide substructure are provided which are solid at standard conditions for temperature and pressure. Surprisingly, the diamide substructure of the amino protecting group facilitates efficient purification by precipitation or crystallization of the amino linker compounds from an apolar solvent mixture. Thus, the provision of the 1,4-diamide substructure in the amino protecting groups makes available amino linker building blocks in solid form at standard conditions for temperature and pressure. Standard conditions for temperature and pressure are defined according to the standards of the International Union of Pure and Applied Chemistry (IUPAC) as a temperature of 0° C. and an absolute pressure of 100 kPa.

Advantageously, the solid state of these 1,4-diamide amino linker building blocks allows for accurate portioning and aliquoting for distribution and storage. Furthermore, the 1,4-diamide substructure favors crystal packing and results in improved stability of 1,4-diamide amino linker building blocks as e.g. according to Formula III presented in FIG. 2. In contrast, structurally closely related amino linker building blocks e.g. according to Formula V in FIG. 2 which are available in the prior art and which comprise a cyclic imide instead of a 1,4-diamide substructure are not solid but instead they are viscous, oily compounds.

In exemplary embodiments of the amino linker building blocks according to Formula III for example, both of the amide groups of the amino protecting group are N-monosubstituted amides providing two hydrogen atoms, one at each amide group, which are available for (inter- and/or intramolecular) hydrogen bonding with the oxygen of another amide group.

Furthermore, the close steric arrangement of the two polar amide groups in the amino linker compounds of the present invention facilitates deprotection (by an intramolecular reaction mechanism) of the protected amino group under standard deprotecting conditions as will be described further below (see also FIG. 5).

The phosphorous activating group is typically a phosphoramidite moiety, generally used in the art of oligonucleotide synthesis. This phosphorous activating group allows the incorporation of the protected amino linker building block at the 5' hydroxyl group of a nucleic acid or nucleic acid derivative molecule.

In exemplary embodiments of protected linker compounds a protected amino linker phosphoramidite building block according to Formula III is provided.

Formula III

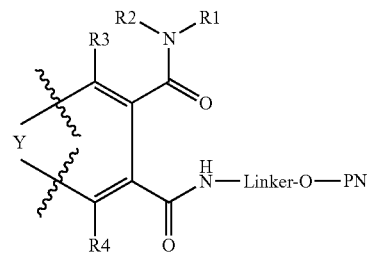

wherein R1 and R2 are independently hydrogen or a substituted C-atom, particularly C1-12 alkyl, or C1-12 alkoxyalkyl, or C1-12 alkyl aryl; more particularly C1-6 alkyl or C1-6 alkoxyalkyl; or more particularly methyl, ethyl, propyl, butyl, pentyl;

wherein R3 and R4 are independently hydrogen, halogen, nitro, $C_{1-4}$ alkyl, $C_{1-4}$ alkoxy or $C_{1-4}$ alkoxyalkyl;

wherein Y is a substructure leading to an aromatic system e.g. according to anyone of the Formulas Y.1 to Formula Y.6

Formula Y.1

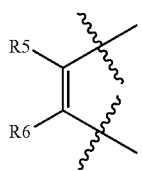

wherein R5 and R6 are independently hydrogen, halogen, nitro, $C_{1-4}$ alkyl, $C_{1-4}$ alkoxy or $C_{1-4}$ alkoxyalkyl;

Formula Y.2

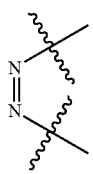

Formula Y.3

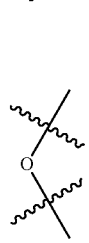

Formula Y.4

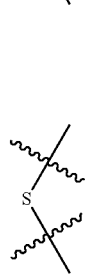

Formula Y.5

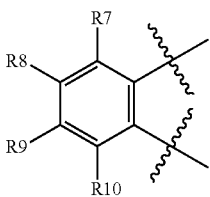

wherein R7 to R10 are independently hydrogen, halogen, nitro, $C_{1-4}$ alkyl, $C_{1-4}$ alkoxy or $C_{1-4}$ alkoxyalkyl;

Formula Y.6

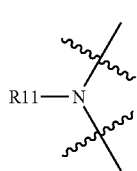

wherein R11 is hydrogen, $C_{1-4}$ alkyl, aryl or $C_{1-4}$ alkoxyalkyl;

wherein PN is a phosphoramidite moiety according to Formula PN:

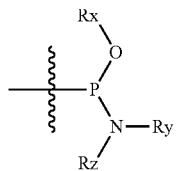

wherein Rx is in particular a methyl or cyanoethyl group and wherein Ry and Rz are in particular independent alkyl-groups comprising one to six C-atoms In embodiments of the amino linker building block according to Formula III-Y.1, R2 to R6 are hydrogen and R1 is hydrogen or a substituted C-atom, particularly $C_{1-12}$ alkyl, or $C_{1-12}$ alkoxyalkyl, or $C_{1-12}$ alkyl aryl; more particularly $C_{1-6}$ alkyl or $C_{1-6}$ alkoxyalkyl; or more particularly methyl, ethyl, propyl, butyl or pentyl.

In embodiments of the amino linker building block according to Formula IX, R2 to R6 are hydrogen, R1 is methyl, and Rx is cyanoethyl and Ry and Rz are isopropyl:

Formula IX

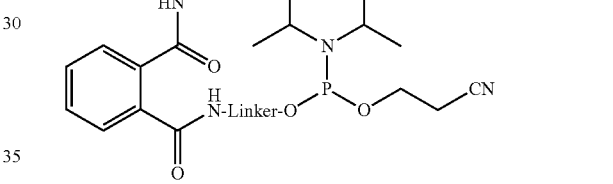

The term linker in the context of this application is defined as a linear or branched hydrocarbon chain which is optionally substituted or interrupted by one or more functional groups and/or heteroatoms and which comprises up to approximately 50 C atoms. The linker connecting the amino protecting group with the phosphorous activating group is selectable according to any particular application within a wide range of sizes and structures. Embodiments of a linker include an essentially linear spacer such as an alkyl chain or an oligoethylenglycol chain. However, within the limits of its applicability as an amino linker building block in the field of nucleic acid synthesis, the chemical structure of the linker is freely selectable. The linker comprises up to approximately 50, or 25 or 15 C atoms. In some embodiments the linker comprises functionalities for further specific applications.

In some embodiments the linker comprises alkyl-, cycloalkyl-, alkyl-aryl-, alkylene-, alkenylene-, aryl-alkylene-, alkynylene-, aryl-alkynylene-, alkoxy-, ether, amide, or oligoethyleneglycol linear or branched linker chain segments and/or substituents and wherein said linker optionally comprises heteroatoms and wherein said linker comprises a total of less than 50 C-atoms, more particularly less than 25 C-atoms or less than 15 C-atoms.

In some embodiments the linker is an alkyl chain, particularly a $C_2$-$C_{24}$ alkyl or heteroalkyl chain, more particularly a $C_3$, $C_6$, $C_7$ or $C_{12}$ alkyl or heteroalkyl chain or a $C_5$-$C_{14}$ cycloalkyl or heterocycloalkyl chain, or an ethylene glycol chain, in particular —$(CH_2CH_2O)nCH_2CH_2$—, in which n=0-8, and more particularly n=3 or n=5, and in which the oligoethylene glycol chain optionally comprises one or more additional hetero atoms.

In the second aspect of the invention a method of preparing amino linker building blocks, in particular protected amino linker phosphoramidite building blocks, is provided, in which a linker is covalently bound to a phosphorous activating group at a first end and to an amino protecting group comprising a diamide substructure at a second end.

Some embodiments of methods of preparing amino linker building blocks comprise a Step A in which a cyclic precursor molecule, e.g a substituted or non-substituted cyclic imide or a cyclic imide-linker molecule is provided or prepared in which the linker is covalently bound to the imide nitrogen.

Furthermore some embodiments of preparing amino linker building blocks comprise a Step B in which a phosphorous activation group is added to an appropriate precursor or intermediate comprising a linker. For example a phosphoramidite group is added to a linker precursor, e.g. by treatment with a phosphoramidochloridite in the presence of a base or with a phosphordiamidite in the presence of an acid.

And further still, some embodiments of methods of preparing amino linker building blocks comprise a ring opening Step C in which a cyclic intermediate e.g. a cyclic imide precursor or intermediate of the amino protecting group is reacted with an amine under controlled conditions to yield a diamide derivative of the corresponding cyclic imide. For example, in the method of preparing amino linker building blocks of Formula IX or of the general Formula III with Y according to Formula Y.1 the corresponding substituted or non-substituted phthalimide precursor is reacted with an amine under controlled conditions.

Exemplary embodiments of the second aspect of the invention are shown in FIG. 2 presenting some exemplary alternative pathways comprising Steps A, B and C for methods of production of an exemplary embodiment of the amino linker building block according to the general Formula III.

Furthermore, some embodiments of methods of preparing amino linker building blocks include a Step D, in which amino linker phosphoramidite building blocks are precipitated or crystallized.

Thus some embodiments of methods of production of protected amino linker phosphoramidite building blocks according to the general Formula III
either comprise the steps of
Step A: providing a hydroxyl linker cyclic imide compound (e.g. according to Formula IV), wherein a linker is covalently bound to a hydroxyl group at one end and wherein another end of the linker is covalently bound to the N-atom of a substituted or non-substituted cyclic imide moiety
Step B: phosphitylating said hydroxyl group (yielding e.g. a compound according to Formula V or according to Formula III)
Step C: opening said cyclic imide moiety by treatment with an amine yielding a diamide (e.g. according to Formula VII or according to Formula III),
Step D: precipitating or crystallizing the phosphitylated linker diamide compound,
wherein Step B either precedes or follows Step C and wherein Step D is performed after performing both Steps B and C.
or they comprise the steps of:
Step A': providing a substituted or non-substituted cyclic imide e.g. according to Formula VI, wherein the imide nitrogen is substituted with R1, e.g. with C1-12 alkyl, or C1-12 alkoxyalkyl, or aryl, particularly with C1-4 alkyl, more particularly with a methyl group
Step C': reacting the cyclic imide with a linker covalently bound to a hydroxyl group at a one end and to an amino group at another end yielding a hydroxy linker diamide compound (e.g. according to Formula VII)
Step B': phosphitylating the hydroxyl group of said hydroxy linker diamide compound yielding a phosphitylated linker diamide compound (e.g. according to Formula III)
Step D: precipitating a phosphitylated linker diamide compound.

A further exemplary embodiment according to the second aspect of the invention is a method of production of protected amino linker phosphoramidite building blocks comprising the following steps: In a first step a phosphitylated linker cyclic imide compound, e.g. a compound according to Formula V, is provided. In a subsequent ring opening as described above in Step C the cyclic imide moiety of the phosphitylated linker cyclic imide compound is opened by treatment with an amine yielding a phosphitylated linker diamide compound (e.g. according to Formula III). Subsequently, the phosphitylated linker diamide compound is precipitated as described above in Step D.

The third aspect of the invention relates to the method of coupling protected linker compounds and more particularly a method of preparing a 5' amino modified nucleic acid e.g. by coupling an amino linker building block to a previously assembled and protected oligonucleotide comprising a free 5'-OH group, followed by oxidation to the corresponding phosphoric acid triester and deprotecting e.g. with methylamine or ammonia/methylamine mixtures in solution or in the gas phase In some embodiments, the method includes the steps of sequentially coupling nucleotides to a solid support to obtain a precursor oligonucleotide with a free 5'-OH group. In a Step 1 the amino linker building block comprising a 1,4-diamide amino protecting group is coupled the precursor oligonucleotide. In Step 2 the 5'-modified oligonucleotide is treated with an amine to release the terminated oligonucleotide and to remove all protecting groups including the diamide amino protecting group which was introduced in Step 1 to form a deprotected 5' amino modified oligonucleotide.

The invention also relates to the coupling product of the amino linker building block coupled to a 5' end position of a nucleic acid or nucleic acid derivative, yielding an amino functionalized nucleic acid or nucleic acid derivative comprising a 1,4-diamide amino protecting group according to Formula VIII in particular an amino protecting group, according to any one of Formulas VIII-Y.1 to VIII-Y6 which is covalently bound via a linker to a 5' end position of a nucleic acid or nucleic acid derivative.

The fourth aspect of the invention relates to the use of a 1,4-diamide protecting group according to Formula VIII for protection of an amino group, particularly of a primary amino group. In particular the fourth aspect of the invention relates to the use of a 1,4-diamide protecting group for the protection of an amino group in a nucleic acid molecule or nucleic acid derivative or more particular to its use at the 5' terminus of a nucleic acid molecule or derivative thereof. Both amide groups of the 1,4-diamide are covalently bound to two neighbouring C-atoms of an aromatic system. These neighbouring C-atoms of the aromatic system constitute the 2- and the 3-position of the 1,4-diamide substructure of the amino protecting group (see Formula II in FIG. 1).

The nitrogen of one of the amide groups is labeled Nx in Formula VIII below. For example in Formula II, and analogously in Formula VIII below, the Nx is bound to the C4 carbon atom, indicating its position relative to the aromatic system and its substituents. However, this choice is arbitrary and Nx is either covalently bound to the C1 or the C4 of the diamide.

This nitrogen Nx is mono-substituted and it constitutes the nitrogen of a protected primary amino group. This primary amino group is covalently bound to a linker of an amino linker compound. In some embodiments this Nx is the nitrogen of an amino linker nucleic acid molecule or derivative thereof. The nitrogen of the other amide group of the 1,4-diamide protecting group is mono- or disubstituted. Thus, the diamide substructure of the amino protecting group provides at least one H atom available for hydrogen bonding. The presence of the two polar amide groups in the amino protecting group particularly favors inter- and intra-molecular hydrogen bonding and leads to favorable physical and chemical properties of compounds comprising the 1,4-diamide protecting group.

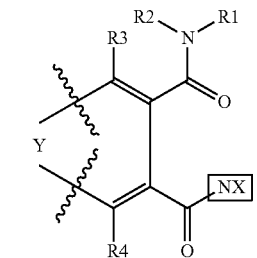

Formula VIII wherein Nx is a nitrogen of a protected primary amino group in a compound x, in particular Nx is part of an amino linker compound or of an amino linker nucleic acid molecule or of a derivative thereof wherein R1 and R2 are independently hydrogen or $C_{1-12}$ alkyl, or $C_{1-12}$ alkoxyalkyl, or $C_{1-12}$ alkyl aryl or in particular methyl, ethyl, propyl, butyl or pentyl, wherein R3 and R4 are independently hydrogen, halogen, nitro, C1-4 alkyl, C1-4 alkoxy or C1-4 alkoxyalkyl; or aryl wherein Y is a substructure e.g. according to anyone of the Formulas Y.1 to Formula Y.5, wherein R5 to R10 are independently hydrogen, halogen, nitro, $C_{1-4}$ alkyl, $C_{1-4}$ alkoxy or $C_{1-4}$ alkoxyalkyl; or to Formula Y.6, wherein R11 is hydrogen, $C_{1-4}$ alkyl, aryl or $C_{1-4}$ alkoxyalkyl Accordingly, exemplary embodiments of 1,4-diamide amino protecting groups include:

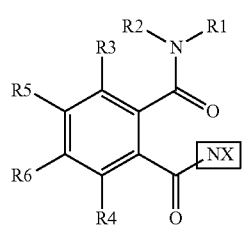

Formula VIII-Y.1

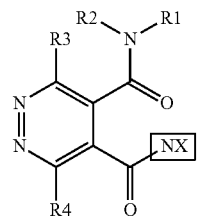

Formula VIII-Y.2

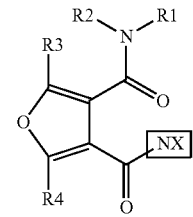

Formula VIII-Y.3

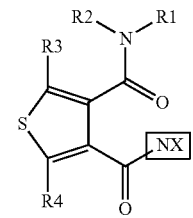

Formula VIII-Y.4

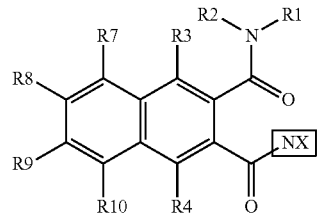

Formula VIII-Y.5

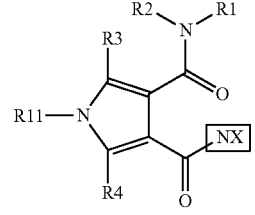

Formula VIII-Y.6

The 1,4-diamide amino protecting groups and the methods as presented here provide convenient and efficient means for the preparation of protected amino linker compounds, which are efficiently introduced into the 5'-position of oligonucleotides, in particular to a previously assembled, immobilized and protected oligonucleotide containing a free 5'-OH group at the 5'-end by standard methods. A particular advantage resulting from the 1,4-diamide substructure of the protecting group is that it makes solid amino linker compounds available. Solid 1,4-diamide amino linker compounds are easily aliquoted and are characterized by improved stability allowing extended storage times compared to linker compounds available in the prior art. A further advantage is that the amino group is finally deprotected at the same time and under the same conditions as the oligonucleotide portion is deprotected and disconnected from a solid support. The resulting 5'-amino modified nucleic acids are used in a multitude of applications, such as in the preparation of dye-containing nucleic acids, reporter group-containing nucleic acids or immobilized nucleic acids.

BRIEF DESCRIPTION OF THE FIGURES

FIG. 6 Pictures of exemplary solid amino linker phosphoramidites according to the general Formula IX, in particular according to Formula XIV, Formula XV and Formula XVI in FIGS. 6A, 6B and 6C, respectively.

FIG. 7 Stability of an exemplary amino linker according to the prior art (Formula I) and according to an embodiment of the invention (Formula XIV) under storage conditions, as measured after the indicated duration of storage at room temperature by 31P-NMR analysis.

DETAILED DESCRIPTION OF THE INVENTION

Reference will now be made in detail to a presently preferred embodiments of the invention, examples of which are fully represented in the accompanying formulas. Such examples are provided by way of explanation of the invention, not as a limitation thereof. In fact, it will be apparent to those skilled in the art various modifications and variations can be made in the present invention without departing from the spirit and scope thereof. For instance, features illustrated or described as part of one embodiment may be used on another embodiment to yield still a further embodiment. Still further, variations and selections of chemicals or materials and/or characteristics may be practiced to satisfy particular desired user criteria. Thus it is intended that the present invention cover such modifications and variations as come within the scope of the present features and their equivalents.

In one exemplary embodiment according to the first aspect of the invention the amino linker compounds has the chemical structure according to Formula IX:

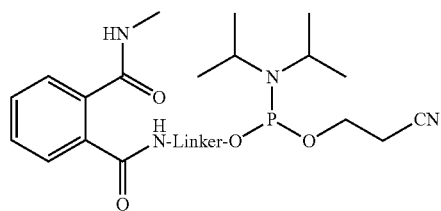

Formula IX

In the amino linker building block according to Formula IX, the amino group is protected by a phthalic diamide group. The amino group is thereby covalently bound via a stable amide bond to the protecting group. Such amino linker building blocks are not soluble in apolar solvents or mixtures of solvents and can therefore easily be precipitated by treating a solution of the compounds in e.g. dichloromethane with an apolar solvent such as hexanes.

In the second aspect of the invention, methods of producing the protected amino linker phosphoramidite building blocks are provided.

Figure 1:
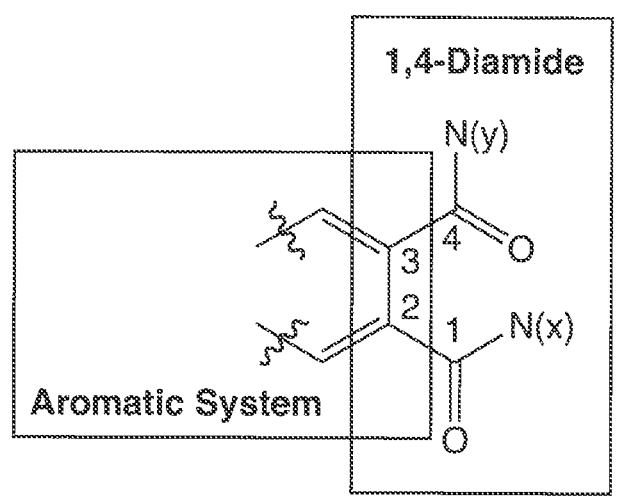
FIG. 1 defines the term "1,4-diamide" with numbering of the involved C-atoms and shows its connection to aromatic systems relevant to the here presented amino protecting groups and amino linker compounds
Figure 2:
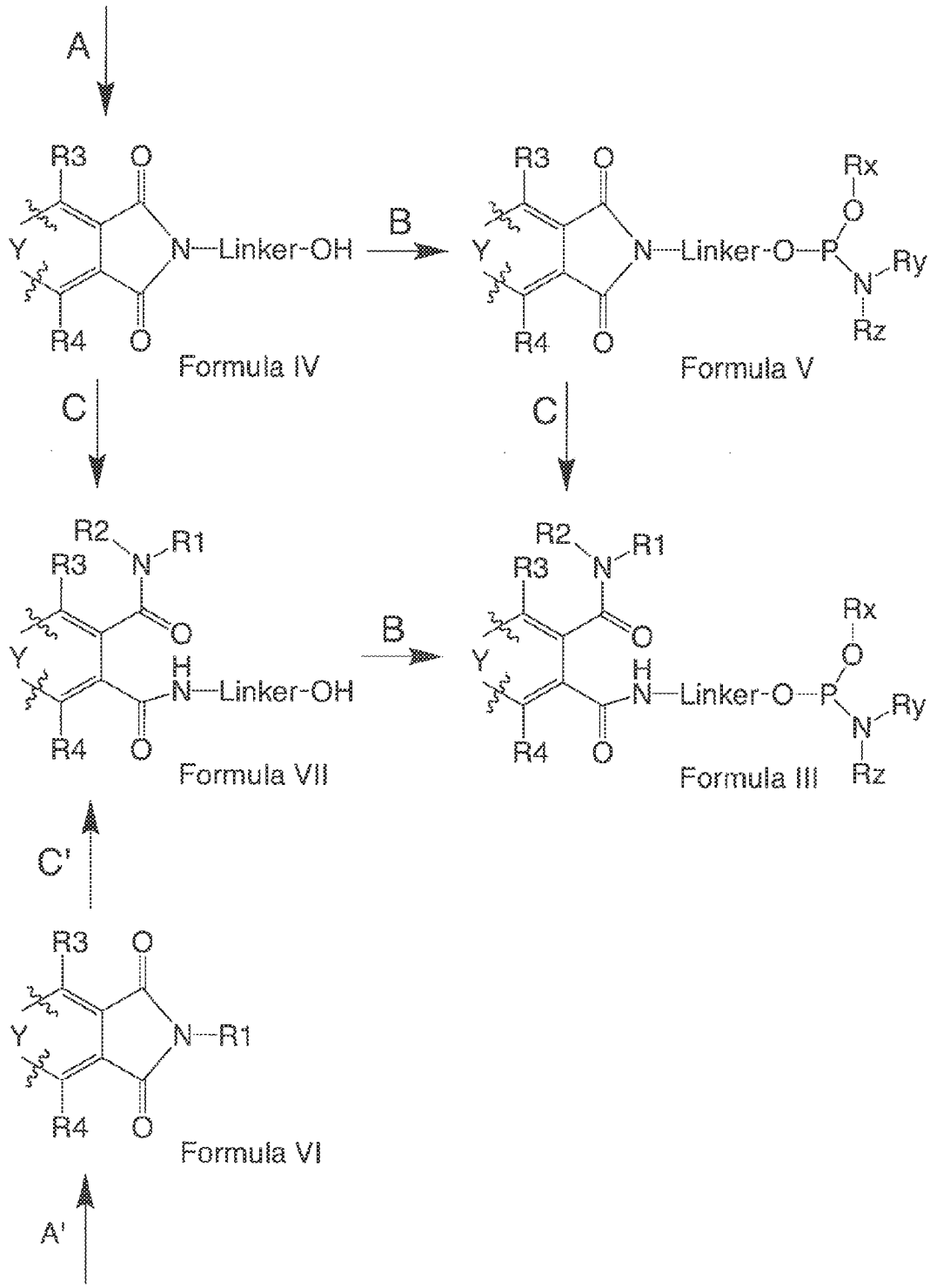
FIG. 2 presents an overview over some exemplary alternative pathways for the method of synthesis of an exemplary embodiment of the amino linker building block according to Formula III.

In FIG. 2 an overview over some exemplary alternative pathways for methods of production of an exemplary embodiment of the amino linker building block according to Formula III is presented. The preparation or provision of an appropriate cyclic precursor molecule is called Step A (some examples are given in FIG. 3). The addition step of a phosphorous activation group, e.g. a phosphoramidite, is called Step B. The ring opening step is called Step C in FIG. 2 (and also in FIG. 3 described further below). As exemplary methods, in two alternative pathways shown in FIG. 2 the sequence of the Steps B and C, i.e. of addition of the phosphoramidite group and of the ring-opening step, is interchanged. As further exemplary method, a third alternative pathway is shown in FIG. 2: a substituted or non-substituted cyclic imide precursor is provided by Step A' and is opened during the reaction with an amino substituted linker alcohol to form a protected amino linker diamide intermediate in Step C' to which in a Step B a phosphoramidite group is added. Furthermore, in a Step D of embodiments of methods of preparing amino linker building blocks, amino linker phosphoramidite building blocks are precipitated or crystallized.

Figure 3:
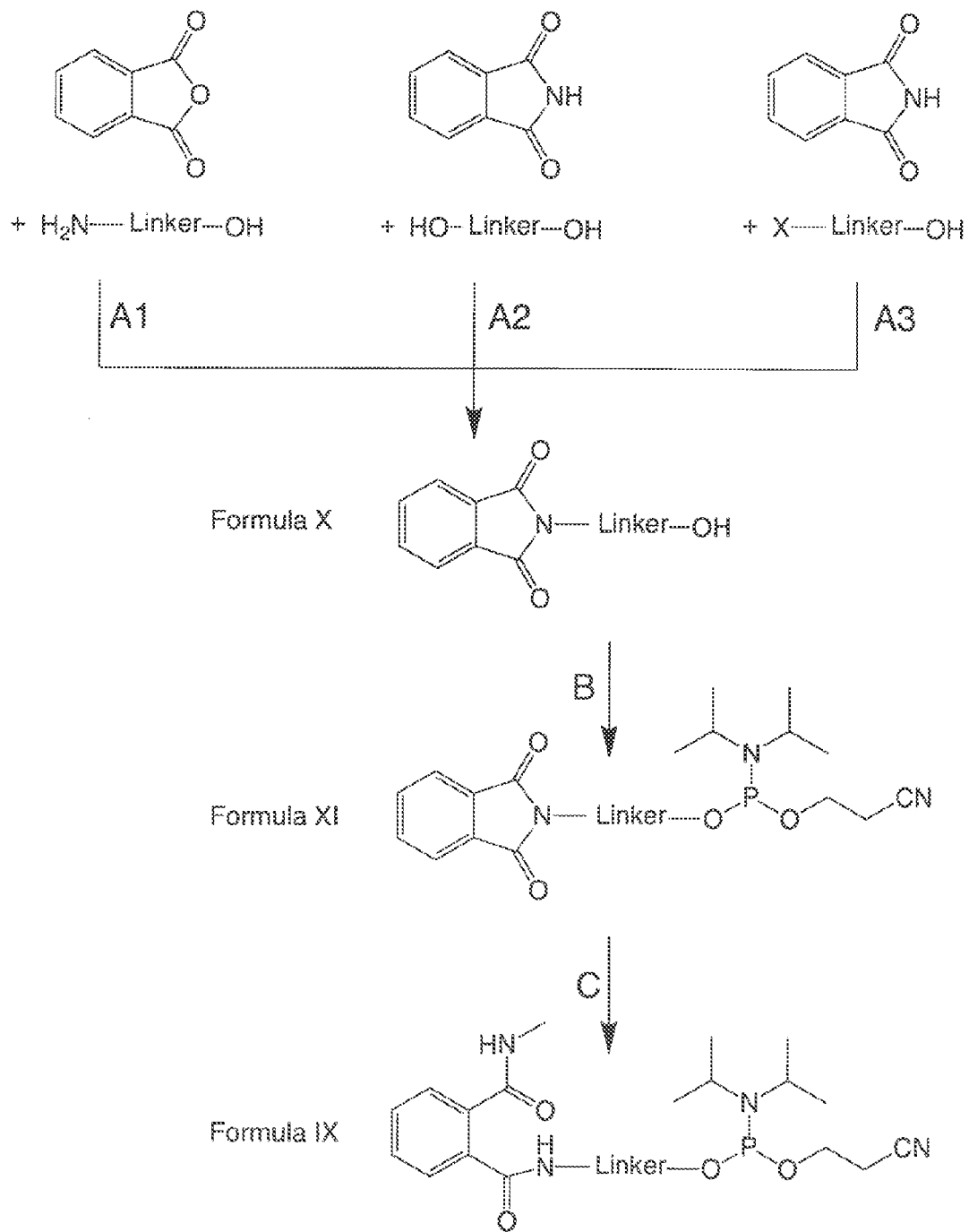
FIG. 3 depicts exemplary embodiments of the methods of production of the amino linker building block according to Formula IX. Methods A1, A2 and A3 are alternatives for the formation of the phthalimide X under various conditions, Step B is the phosphitylation with 2-cyanoethyl diisopropylphosphoramidochloridite and N-ethyl-N,N-diisopropylamine in dichloromethane, and Step C is the ring-opening with methylamine in methanol, followed by precipitation of product according to Formula IX in dichloromethane/hexanes.

In FIG. 3 exemplary embodiments of the methods of production of 5' protected amino linker phosphoramidite building blocks according to Formula IX are further detailed. In particular, examples of Step A with exemplary formation of a hydroxyl linker-phthalimide compound, N-(hydroxyalkyl)phthalimide (according to Formula X) is outlined according to e.g method A1 or method A2 or method A3 under various, well-known conditions is formed as described below:

A1) From the cyclic anhydride of a suitable substituted benzene 1,2-dicarboxylic acid (e.g. unsubstituted or substituted phthalic anhydride) which is treated with an amino alcohol ($H_2$N-Linker-OH) in a high-boiling solvent capable of removing water azeotropically, typically toluene. At the reflux temperature of toluene, the corresponding cyclic phthalimide is formed and the bye-product water is removed azeotropically. A2) From the cyclic imide of a suitable substituted benzene 1,2-dicarboxylic acid (e.g. unsubstituted or substituted phthalimide) which is treated with a diol (HO-Linker-OH) under Mitsunobu conditions (dialkyl azodicarboxylate and triphenylphosphine in THF). A3) From the cyclic imide of a suitable substituted benzene 1,2-dicaboxylic acid (e.g. unsubstituted or substituted phthalimide) which is deprotonated with a strong base (e.g. KOH or NaH) and alkylated with a halogenated alcohol (X-Linker-OH).

FIG. 3 further shows an exemplary phosphitylation step B, in which Alcohol X, N-(hydroxyalkyl)phthalimide, is then transformed into the corresponding phosphoramidite XI by treatment with an phosphoramidochloridite in the presence of a base or with an phosphordiamidite in the presence of an acid. In a further exemplary ring opening Step C the imide XI is treated with an amine to obtain the amino linker building block IX.

In FIGS. 2 and 3, reference has been made to presently preferred embodiments of the invention, examples of which are fully represented in the accompanying formulas. However, such examples are provided by way of explanation of the invention and not limitation thereof. Analogous methods to those presented in FIGS. 2 and 3 for the production of the exemplary protected linker compound according Formula IX are readily available for the production of other embodiments of amino linker compounds according to Formula III by appropriate selection of the substituents, of the cyclic precursor and of the specific linker and of the specific phosphoramidite moiety according to a specifically desired embodiment of a Formula III protected linker compound. For example, analogous methods of production for synthesizing amino linker building blocks are also applicable to cyclic imides other than to substituted or non-substituted phthalimides. Variations and combinations of different embodiments are within the scope of the invention.

The third aspect of the invention relates to the method of coupling protected linker compounds and more specifically to the coupling of protected amino linker phosphoramidite building blocks to a nucleic acid molecule or derivative thereof and furthermore to the deprotection of the protected amino group removing the amino protecting group off the nucleic acid molecule or derivative thereof.

In an exemplary method of preparing a 5'-amino modified nucleic acid, a building block of the exemplary Formula IX is coupled to a previously assembled, immobilized and protected oligonucleotide containing a free 5'-OH group at the 5'-end, followed by oxidation to the corresponding phosphoric acid triester and deprotecting with methylamine or ammonia/methylamine mixtures in solution or in the gas phase.

Figure 4:
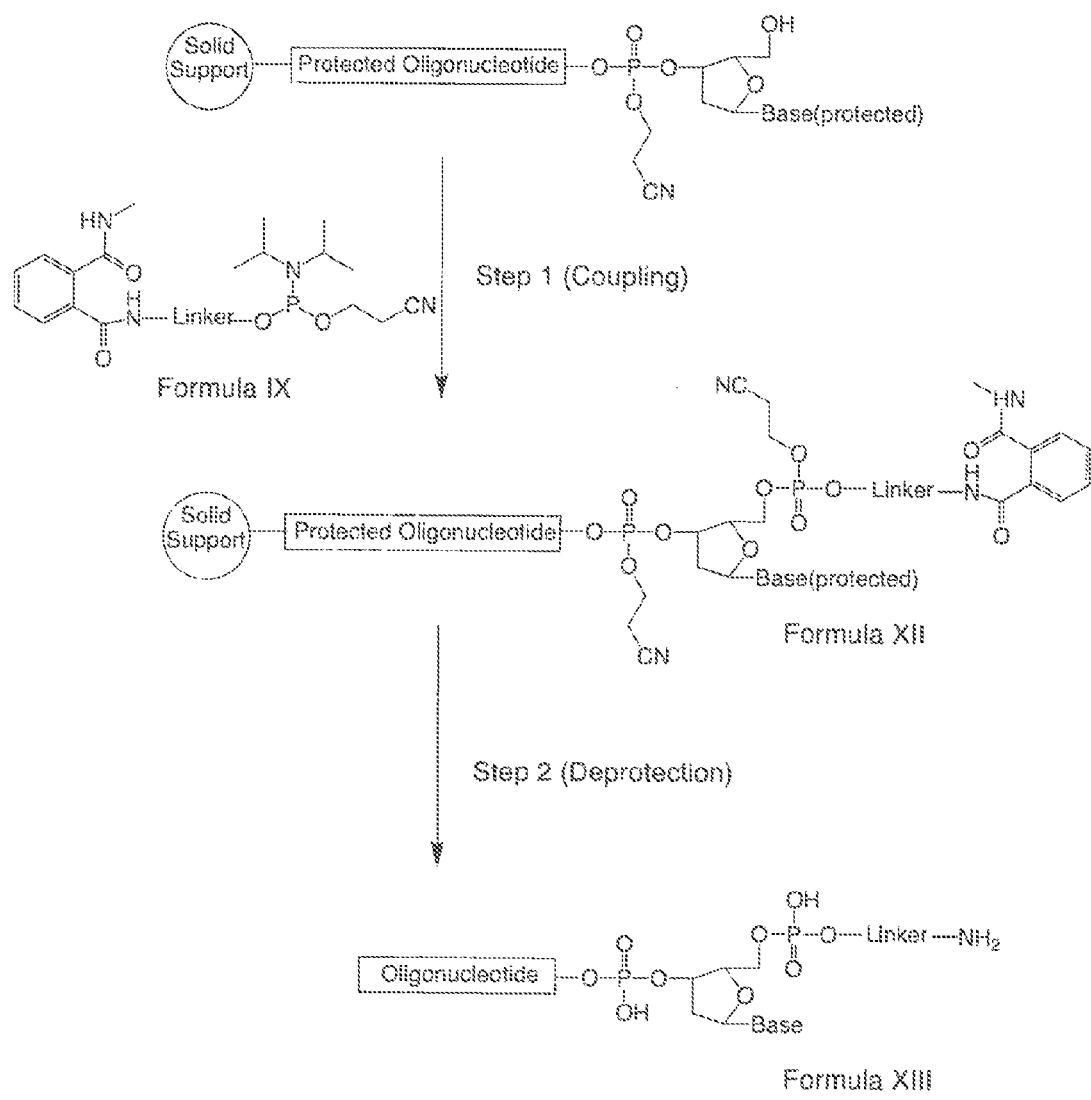
FIG. 4 presents an overview of an exemplary coupling of a exemplary protected amino linker phosphoramidite building block according to Formula IX to a protected and immobilized nucleic acid molecule in Step 1 followed by deprotection of the 5' amino group, in Step 2, resulting in the formation of a 5'-amino linker modified DNA oligonucleotide according to Formula XIII.

In FIG. 4 an exemplary method of preparing a 5' amino modified nucleic acid according to Formula XIII by coupling an exemplary protected amino linker phosphoramidite building block of formula IX to a previously assembled, immobilized and protected nucleic acid molecule containing a free 5'-OH group at the 5' end in Step 1. In subsequent Step 2 deprotection of the protected amino group of this intermediate XII is shown according to the following disclosed methodologies:

In Step 1, the protected amino linker phosphoramidite building block is coupled on a nucleic acid synthesizer comprising the individual steps (i), (ii) and (iii) wherein the sequence of steps (ii) and (iii) is interchangeable:

(i) Coupling reaction to an immobilized, protected oligonucleotide containing a free 5'-OH group. This reaction is typically carried out in an aprotic polar solvent, such as acetonitrile, and in the presence of a weak H—N acid, such as a (substituted) tetrazole or imidazole.

(ii) Capping of the unreacted 5'-OH group and cleavage of undesired coupling products at nucleobase moieties with an acid anhydride in the presence of a catalyst, e.g. acetic acid anhydride and N-methyl imidazole in tetrahydrofuran (THF) or acetonitrile (ACN).

(iii) Oxidation of the resulting phosphite triester to the corresponding phoshoric acid triester by oxidizing agents such as $I_2/H_2O$ in pyridine/THF (or ACN) mixtures.

Figure 5:
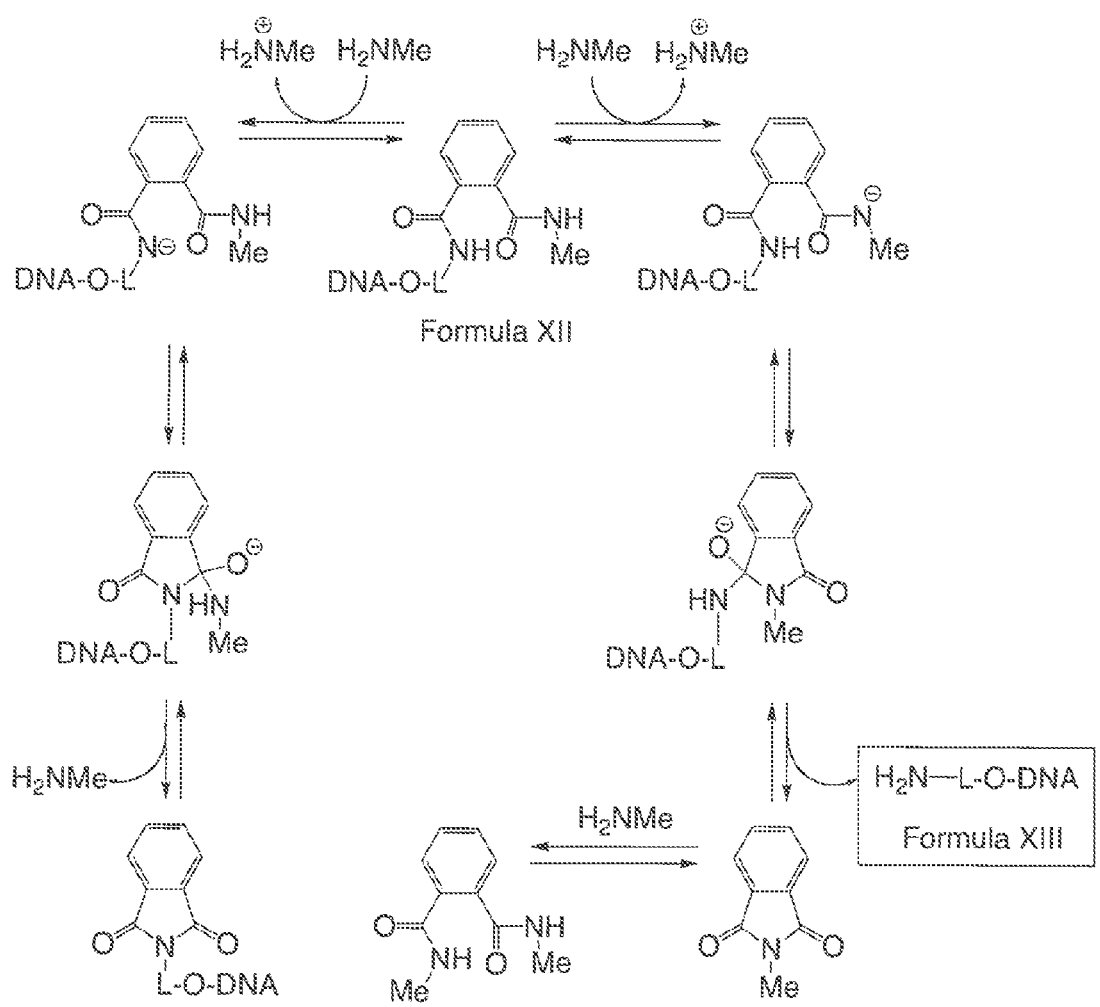
FIG. 5 shows the deprotection mechanism of an exemplary protected amino linker group covalently bound to a DNA molecule under exemplary conditions with methylamine (L=linker).

Step 2 in FIG. 4 is the deprotection reaction which removes not only the amino protecting group but simultaneously also removes all nucleobase and phosphate protecting groups and additionally cleaves the 5'-amino modified oligonucleotide from the solid support. This reaction is carried out e.g. with ammonia or advantageously with methylamine or ammonia/methylamine mixtures (AMA) in water, in alcohol/water mixtures or in the gas phase. The removal of the diamide amino linker protecting group is triggered by deprotonation of an amide group, followed by intramolecular attack of the resulting nucleophilic deprotonated nitrogen at the neighbouring carbonyl group, formation of a tetrahedral intermediate and finally elimination of an amine and formation of a cyclic imide. This compound will react with another amine, e.g. methylamine, thereby forming again a N,N'-dialkyl diamide, e.g. N,N'-dimethyl phthalic diamide as shown exemplary in FIG. 5. All steps are fully reversible and therefore, a large excess of methylamine will lead finally to the formation of N,N'-dimethyl phthalic diamide and the deprotected amino group of the 5' amino modified oligonucleotide XIII.

EXAMPLE 1 a) Preparation of N-methyl-N'-(ω'-hydroxyalkyl)phthalic diamide ω'-(2-cyanoethyldiisopropylphosphoramidite) (Formula IX): General procedure (see FIG. 3)

To a solution of 0.1 mol N-(ω'-hydroxyalkyl)phthalimide (Formula X) and 25.8 g (0.2 mol)N-ethyl-N,N-diisopropylamine in 400 ml dichloromethane was added slowly 30.7 g (0.13 mmol) 2-cyanoethyl diisopropylphosphoramidochloridite. After 2 h at 25°, the reaction mixture was treated with $H_2O$ and stirred vigorously for 5 min. The phases were separated and the organic phase was dried ($Na_2SO_4$) and evaporated to dryness. The oily residue was subjected to silica gel chromatography (ethyl acetate/hexanes+2% $Et_3N$ as mobile phase). The intermediate (Formula XI) was dissolved in 200 ml MeOH and treated with 25 ml $MeNH_2$ in EtOH (8 M, 0.2 mol). After 10 min at 25°, the mixture was evaporated, dissolved in dichloromethane and extracted with $H_2O$. After phase separation, the organic phase was dried ($Na_2SO_4$) and evaporated to dryness. The resulting solid product (Formula IX) was recrystallized from dichloromethane/hexanes and dried in vacuo.

b) Preparation of N-methyl, N'-(6'-hydroxyhexyl)phthalic diamide 6'-(2-cyanoethyl diisopropylphosphoramidite) Formula XIV (with a —C₆H₁₂— linker)

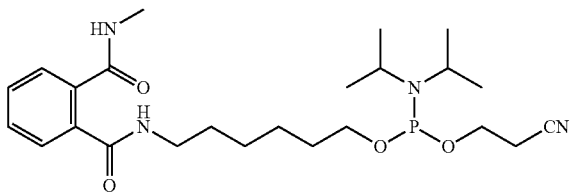

Formula XIV

Prepared according to the general procedure (see above) from 24.7 g N-(6-hydroxyhexyl)phthalimide [S. Neelakantan, I. Surjawan, H. Karacelik, C. L Hicks, P.A. Crooks, Bioorg. & Med. Chem. Lett. 2009, 5722]. Yield: 26.8 g (60%) as white solid (see FIG. 6A).

¹H-NMR (300 MHz, CDCl₃): 7.57, 7.44 (2 m, 2×2 H, ArH); 6.94 (br. q, J=ca. 5 Hz, 1 H, NHMe); 6.85 (br. t, J=ca. 6 Hz, 1 H, NHCH₂); 3.92-3.73 (m, 2 H, 2×NCH(Me)₂); 3.73-3.53 (m, 4 H, 2×CH₂OP); 3.38 (q, J=ca. 7 Hz, 2 H, NHCH₂); 2.94 (d, J=4.9 Hz, 3 H, NHCH₃); 2.64 (t, J=6.5 Hz, 2 H, CH₂CN); 1.70-1.53 (m, 4 H, 2×CH₂); 1.45-1.35 (m, 4 H, 2×CH₂); 1.19 (2 d, J=6.9, 12 H, 2×C(CH₃)₂). ³¹P-NMR (121 MHz, CDCl₃, ¹H-decoupled): 148.5.

c) Preparation of N-methyl, N'-(12'-hydroxydodecanyl) phthalic diamide 12'-(2-cyanoethyl diisopropylphosphoramidite) Formula XV (with a —C₁₂H₂₄— linker)

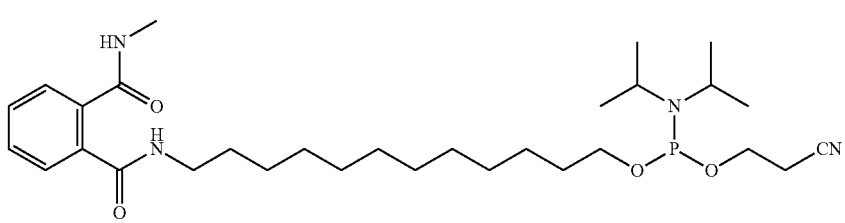

Formula XV

Prepared according to the general procedure (see above) from 33.1 g N-(12-hydroxydodecyl)phthalimide [I. Sprung, A. Ziegler, S. L. Flitsch, Chem. Comm. 2002, 2676]Yield: 34.5 g (65%) as white solid (see FIG. 6B).

¹H-NMR (300 MHz, CDCl₃): 7.54, 7.42 (2 m, 2×2 H, ArH); 7.05 (br. q, J=ca. 5 Hz, 1 H, NHMe); 6.90 (br. t, J=ca. 6 Hz, 1 H, NHCH₂); 3.92-3.74 (m, 2 H, 2×NCH(Me)₂); 3.72-3.51 (m, 4 H, 2×CH₂OP); 3.35 (q, J=ca. 7 Hz, 2 H, NHCH₂); 2.93 (d, J=4.9 Hz, 3 H, NHCH₃); 2.65 (t, J=6.8 Hz, 2H, CH₂CN); 1.67-1.50 (m, 4 H, 2×CH₂); 1.41-1.24 (m, 16 H, 8×CH₂); 1.19 (2 d, J=6.8, 12 H, 2×C(CH₃)₂). ³¹P-NMR (121 MHz, CDCl₃, ¹H-decoupled): 148.5.

d) Preparation of N-methyl, N'-(11'-hydroxy-3',6',9'-trioxaundecanyl)phthalic diamide 11'-(2-cyanoethyl diisopropylphosphoramidite) Formula XVI (with a —CH₂CH₂OCH₂CH₂OCH₂CH₂OCH₂CH₂— linker)

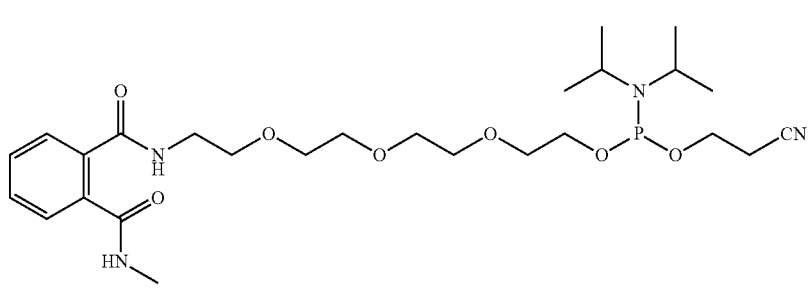

Formula XVI

Prepared according to the general procedure (see above) from 32.3 g N-(11'-hydroxy-3',6',9'-trioxaundecanyl)phthalimide [J. Kim, T. Morozumi, H. Nakamura, Org. Lett. 2007, 4419]. Yield: 32.9 g (63%) as white solid (see FIG. 6C).

$^1$H-NMR (300 MHz, CDCl$_3$): 7.66, 7.53 (2 m, 2×1 H, ArH); 7.46 (m, 2 H, ArH); 7.00 (br. s, 1 H, NHMe and NHCH$_2$); 3.92-3.53 (m, 20 H, 2×NCH(Me)$_2$, 2×CH$_2$OP, NHCH$_2$, 6×CH$_2$); 2.95 (d, J=4.7 Hz, 3 H, NHCH$_3$); 2.64 (t, J=6.4 Hz, 2 H, CH$_2$CN); 1.70-1.53 (m, 4 H); 1.45-1.35 (m, 4 H, 2×CH$_2$); 1.18 (2d, J=6.8, 12 H, 2×C(CH$_3$)$_2$). $^{31}$P-NMR (121 MHz, CDCl$_3$, $^1$H-decoupled): 149.7.

EXAMPLE 2

Experiment for the Determination of Stability Under Storage Conditions

From Sigma-Aldrich a 250 mg sample of 6-amino-N-trifluoroacetyl-hexan-1-ol 1-(2-cyanoethyl diisopropylphosphoramidite) (Formula I) was ordered which arrived on dry ice. As soon as it arrived, the colorless, oily compound was stored at room temperature in the dark. At the same time, a solid 250 mg sample of N-methyl, N'-(6'-hydroxyhexyl) phthalic diamide 6'-(2-cyanoethyl diisopropylphosphoramidite) Formula XIV (previously stored for 6 weeks at −20°) was placed in an identical bottle and stored under identical conditions. After reaching room temperature, 20 mg of both compounds were withdrawn, dissolved in 0.7 ml CDCl$_3$ and subjected to $^{31}$P-NMR analysis (see FIG. 7). Immediately after withdrawal, the two bottles were capped and again stored at room temperature. After 1 day and 7 days, respectively, the same analysis was repeated (see FIG. 7). According to these measurements, the oily TFA-protected aminolinker phosphoramidite (Formula I) had a purity of 92%, 75% and 10% after t=0, 1 day and 7 days, respectively. In contrast, the solid pthalic diamide protected aminolinker phosphoramidite (Formula XIV) according to the present invention was completely stable for the duration of 7 days as revealed by $^{31}$P-NMR analysis (121 MHz, CDCl$_3$), measured after the indicated duration of storage at room temperature shown in FIG. 7.

EXAMPLE 3

Experiment for the Determination of Deprotection Conditions

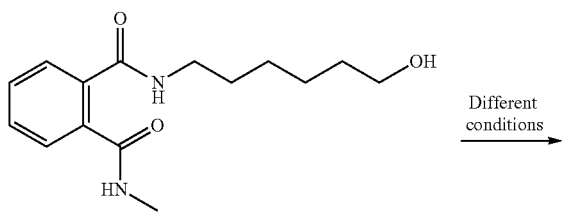

Different conditions →

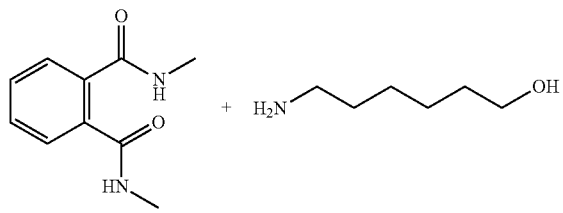

Figure 8:
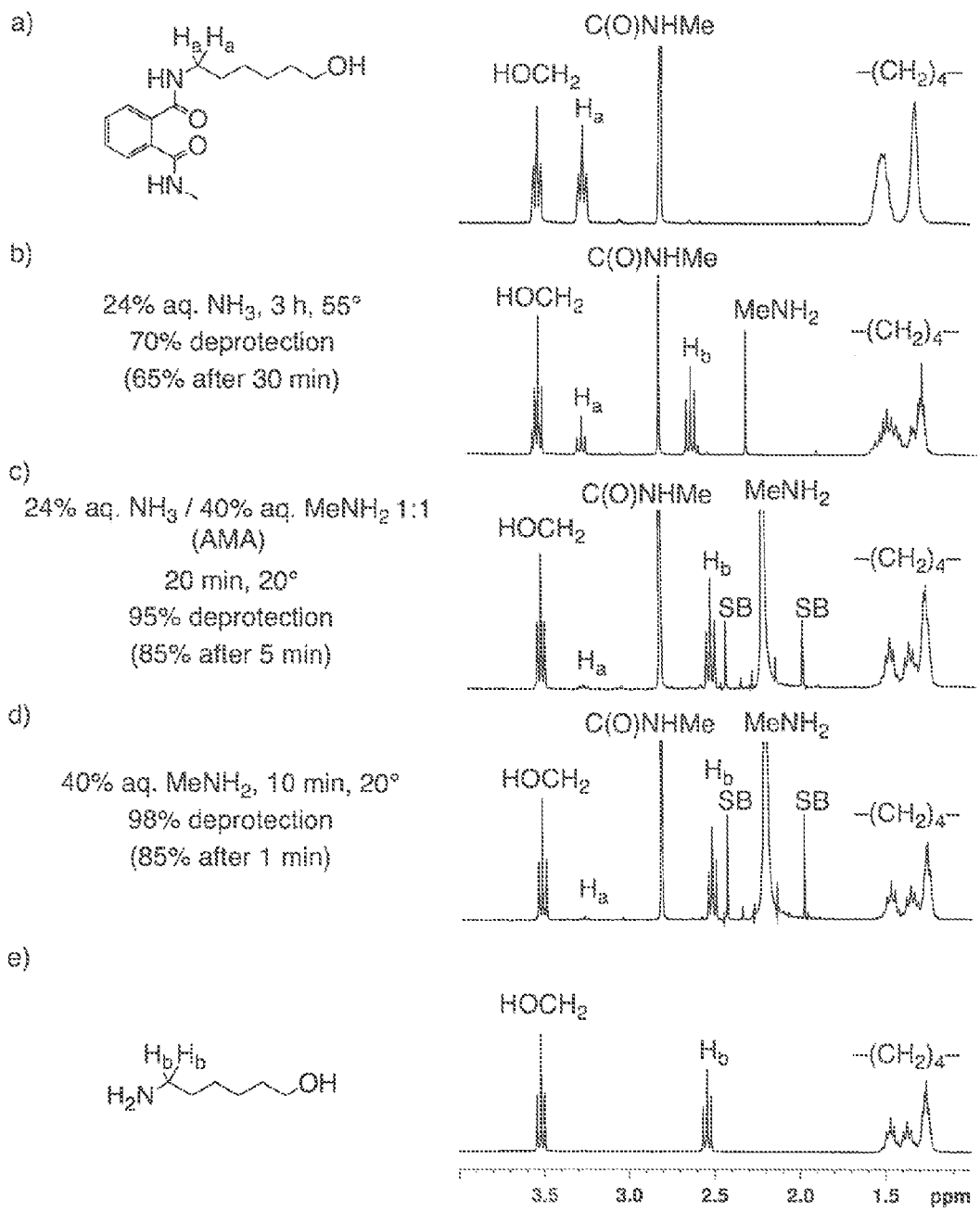
FIG. 8 gives an overview over the results of the deprotection reaction of a model diamide compound under the indicated conditions by 1H-NMR spectroscopy (300 MHz) in D2O.

Samples of 50 mg N-methyl, N'-(6'-hydroxyhexyl) phthalic diamide were dissolved in 1 ml deprotection solution (as indicated in FIG. 8) and incubated under the variable conditions b), c) and d). After different time intervals, 0.1 ml aliquots were withdrawn, diluted with 0.6 ml D$_2$O and analyzed by $^1$H-NMR. The spectra were compared with those from a) the starting material and e) 6-amino hexanol, respectively (see FIG. 8).

Almost quantitative deprotection within <30 min occurred at 20° under conditions c) and d), i.e. by 40% aq. MeNH$_2$ and by 24% aq. NH$_3$/40% MeNH$_2$ 1:1 (AMA), respectively. In contrast, a two-phase process was observed at condition b) by 24% aq. NH$_3$ at 55°: after 30 min 65% were deprotected and after 3 h 70%, respectively. Under these conditions, the direct elimination of the linker amine from the methyl substituted starting material (according to the upper processes in FIG. 5) seems to be fast, whereas the elimination of the linker amine from the NH$_2$-derivative (obtained with ammonia according to the lower processes in FIG. 5) seems to be slow.

FIG. 8 gives an overview over the results of the deprotection reaction under the tested conditions by $^1$H-NMR spectroscopy (300 MHz) in D$_2$O. Shown are partial spectra (1.0-4.0 ppm): a) Spectrum of starting material. b, c, d): Right side—Spectra of reaction mixtures, diluted with D$_2$O and recorded after the indicated time; Left side—reaction conditions and results. e) Spectrum of the product. S: $^{13}$C-satellite signals from the MeNH$_2$ signal.

EXAMPLE 4

Synthesis of a DNA Sequence with a 5'-Amino Linker and its Conjugation to Digoxigenine

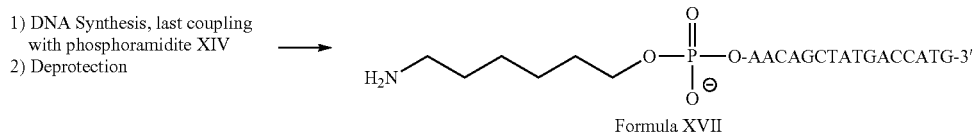

Formula XVII

↓ Digoxigenine-NHS ester

-continued

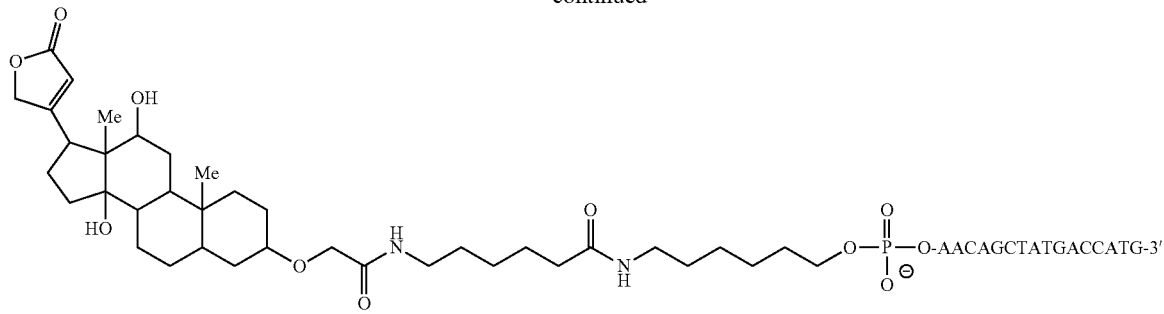

Figure 9:
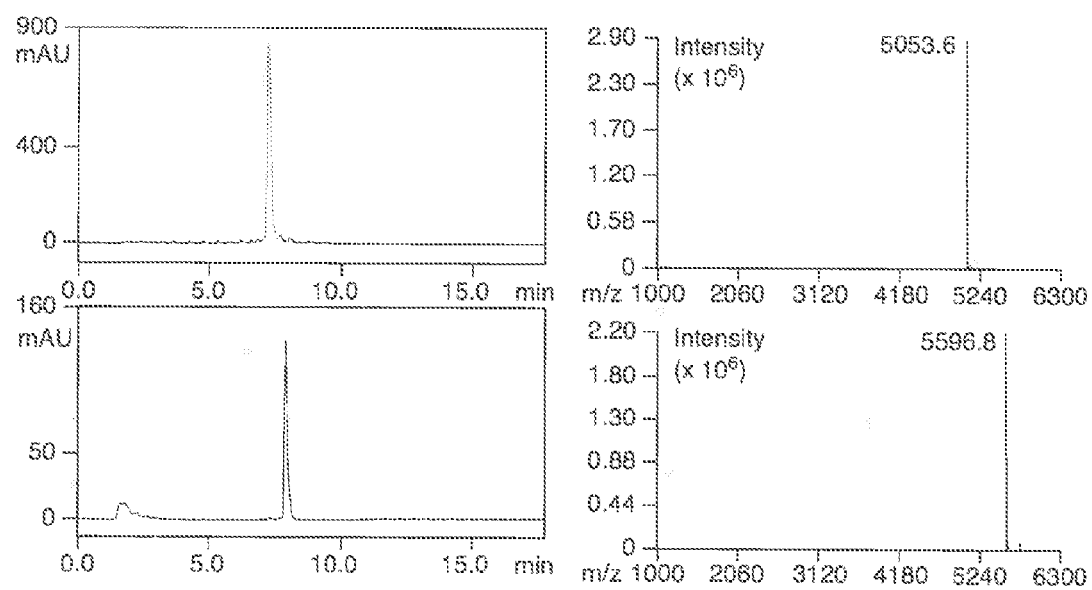
FIG. 9 shows HPLC traces (left) and ESI MS spectra (right) of a crude 5'-aminolinker DNA sequence (Formula XVII) (top) and its crude digoxigenine conjugate (Formula XVIII) (bottom).

Formula XVIII a) General: DNA assembly under standard conditions (see S. Pitsch, P. A. Weiss, L. Jenny, A. Stutz, X. Wu, Helv. Chim. Acta 2002, 84, p. 3773) on a Pharmacia Gene Assembler. Reagents and solvents from Sigma Aldrich; DNA phosporamidites, dG CPG solid support and activator (ethyl thiotetrazole) from Glen Research; analytical ion exchange HPLC conditions (see S. Pitsch, P.A. Weiss, L. Jenny, A. Stutz, X. Wu, Helv. Chim. Acta 2002, 84, p. 3773) (gradient 10-60% B in 12.5 min); ESI-MS from Finnegan. TEAA buffer—triethylammonium acetate buffer pH 7.0; ACN—acetonitrile.

b) DNA synthesis: The DNA sequence 5'-(aminolinker) AACAGCTATGACCATG-3' (Formula XVII) was assembled on a 0.2 μmol synthesis scale. The final coupling was carried out with the amino linker building block N-methyl, N'-(6"-hydroxyhexyl)phthalic diamide 6'-(2-cyanoethyldiisopropylphosphoramidite) Formula XIV (with a —$C_6H_{12}$— linker) (c=0.07 M in ACN, 120 μl). Deprotection was carried out with $MeNH_2$ in $H_2O$ (12 M) for 75 min h at 35°. After evaporation, the crude sequence Formula XVII (40 oD) was characterized by HPLC and ESI-MS (see FIG. 9, top). HPLC: $t_R$ 7.24 min (89%) ESI-MS: 5053.6 amu (calc. 5053.4 amu)

c) Counterion exchange: An amount of 35 oD of the above described crude 5'-aminolinker containing DNA sequence Formula XVII in the methylammonium form was loaded onto a $C_{18}$-Sepak cartridge (Waters, pretreated with ACN and 0.2 M TEAA buffer). After washing with 5 ml 0.2 M TEAA buffer and 5 ml $H_2O$, the product sequence was eluted with 2 ml ACN/$H_2O$ 1:1. After evaporation, 32 oD of the DNA sequence Formula XVII in the triethylammonium form were obtained.

d) Conjugation: The above obtained 32 oD DNA sequence XVII in the triethylammonium form were dissolved in 50 μl aqueous borate buffer (0.1 M, pH 8.4) and treated with a solution of 1 mg digoxigenine NHS ester (Sigma) in 100 μl DMF. After 45 min at 30°, the mixture was diluted with 0.9 ml $H_2O$ and subjected to desalting on a NAP 10 column (Pharmacia) according to the manufacturer's instructions. After evaporation, the crude digoxigenine labeled DNA sequence Formula XVIII (27 oD) was characterized by HPLC and ESI-MS. HPLC: $t_R$ 8.01 min (98%); ESI-MS: 5596.8 amu (calc. 5596.9 amu). FIG. 9 shows HPLC traces (left) and ESI MS spectra (right) of the crude 5'-amino linker DNA sequence Formula XVII (top) and its crude digoxigenine conjugate Formula XVIII (bottom).

Although preferred embodiments of the invention have been described using specific terms and devices, such description is for illustrative purposes only. The words used are words of description rather than of limitation. It is to be understood that changes and variations may be made by those of ordinary skill in the art without departing from the spirit of the scope of the present invention, which is set forth in the following claims. In addition, it should be understood that aspects of various other embodiments may the interchanged both in whole or in part. Therefore, the spirit and scope of the appended claims should not be limited to the description of the preferred version contained herein.

What is claimed is:

1. An amino linker building block suitable for preparing 5' amino-modified oligonucleotides comprising a linker covalently bonded between a phosphoramidite moiety and an amino protecting group, wherein the amino protecting group comprises a 1,4-diamide substructure, with two amide groups comprising a C1 and a C4 carbon atom of the 1,4-diamide substructure, wherein the 1,4 diamide substructure is part of an aromatic system in which two neighboring carbon atoms of the aromatic system constitute a 2- and 3- position of the 1,4-diamide substructure, and wherein a nitrogen of one of the amide groups is covalently bonded to the linker and the nitrogen of the other of the two amide groups is not bonded to the linker.

2. An amino linker building block according to claim 1 wherein both of the amide groups are N-mono-substituted amides comprising a hydrogen atom at each amide nitrogen.

3. The amino linker building block of claim 2, wherein the amino linker is a solid.

4. An amino linker building block having the structure of Formula III:

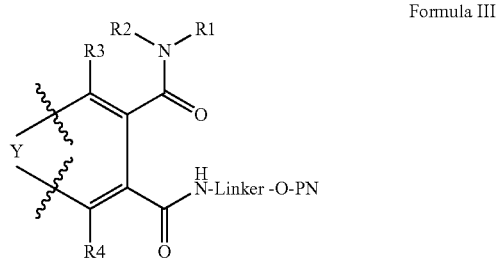

Formula III wherein R1 and R2 are independently hydrogen or a substituted C-atom;
wherein R3 and R4 are independently hydrogen, halogen, nitro, $C_{1-4}$ alkyl, $C_{1-4}$ alkoxy or $C_{1-4}$ alkoxyalkyl;
wherein the linker is a linear or branched hydrocarbon chain which is optionally substituted or interrupted by one or more functional groups and/or hetero atoms and wherein the linker comprises up to 50 C atoms;

wherein PN is the phosphoramidite moiety bonded to the linker and having the structure:

wherein Rx is a methyl or cyanoethyl group and wherein Ry and Rz are independent alkyl-groups comprising one to six C-atoms; and wherein Y is a substructure leading to an aromatic system selected from one of the substructures according to Formulas Y.1 to Y.6

Formula Y.1 wherein R5 and R6 are independently hydrogen, halogen, nitro, $C_{1-4}$ alkyl, $C_{1-4}$ alkoxy or $C_{1-4}$ alkoxyalkyl;

Formula Y.2

Formula Y.3

Formula Y.4

Formula Y.5 wherein R7 to R10 are independently hydrogen, halogen, nitro, $C_{1-4}$ alkyl, $C_{1-4}$ alkoxy or $C_{1-4}$ alkoxyalkyl;

Formula Y.6 wherein R11 is hydrogen, $C_{1-4}$ alkyl, aryl or $C_{1-4}$ alkoxyalkyl.

5. The amino linker building block according to claim 4, wherein the linker comprises alkyl-, cycloalkyl-, alkylaryl-, alkylene-, alkenylene-, aryl-alkylene-, alkynylene-, aryl-alkynylene-, alkoxy-, ether, amide or oligoethyleneglycol linear or branched linker chain segments and/or substituents and wherein said linker optionally comprises heteroatoms and wherein said linker comprises a total of less than 50 C-atoms.

6. The amino linker building block according to claim 4, wherein the linker is an aliphatic chain selected from the group consisting of an alkyl chain and a heteroalkyl chain.

7. The amino linker building block according to claim 6, wherein R2 to R6 are hydrogen (Formula III-Y.1) and R1 is hydrogen or a substituted C-atom.

8. The amino linker building block according to claim 4, wherein R2 to R6 are hydrogen, R1 is methyl, and wherein Rx is cyanoethyl and Ry and Rz are isopropyl.

9. The amino linker building block of claim 1 wherein the amino linker building block is a solid.

10. The amino linker building block according to claim 9, wherein the 1,4-diamide substructure is part of an aromatic system, in which two neighbouring C-atoms of the aromatic system constitute a 2-and a 3-position of the 1,4-diamide substructure.

11. The amino linker of claim 4, having the structure according to Formula XIV:

12. The amino linker of claim 4, having the structure according to Formula XV:

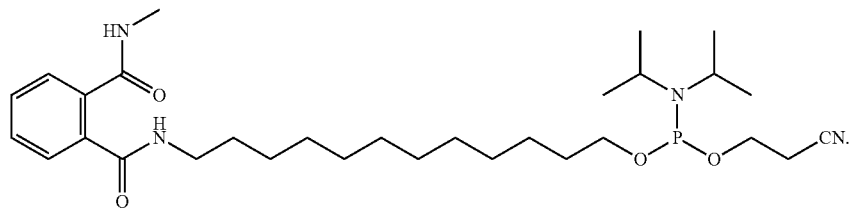 [SMILES: CNC(=O)c1ccccc1C(=O)NCCCCCCCCCCCCOP(OCCC#N)N(C(C)C)C(C)C]

13. The amino linker of claim 4, having the structure according to Formula XVI:

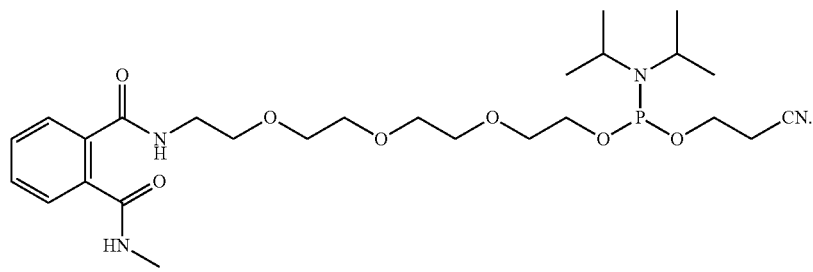 [SMILES: CNC(=O)c1ccccc1C(=O)NCCOCCOCCOCCOP(OCCC#N)N(C(C)C)C(C)C]

14. The amino linker building block of claim 4, wherein $R_1$ and $R_2$ are independently $C_{1-12}$ alkyl, or $C_{1-12}$ alkoxyalkyl, or $C_{1-12}$ alkyl aryl.

15. The amino linker building block of claim 14, wherein $R_1$ and $R_2$ are independently $C_{1-6}$ alkyl or $C_{1-6}$ alkoxyalkyl.

16. The amino linker building block of claim 14, wherein $R_1$ and $R_2$ are independently methyl ethyl, propyl, butyl or pentyl.

17. The amino linker building block of claim 5, wherein the linker comprises less than 25 C-atoms.

* * * * *